(12) United States Patent
Pless

(10) Patent No.: US 8,283,793 B2
(45) Date of Patent: Oct. 9, 2012

(54) DEVICE FOR ENERGY HARVESTING WITHIN A VESSEL

(75) Inventor: Benjamin David Pless, Atherton, CA (US)

(73) Assignee: Autonomic Technologies, Inc., Redwood City, CA (US)

( * ) Notice: Subject to any disclaimer, the term of this patent is extended or adjusted under 35 U.S.C. 154(b) by 643 days.

(21) Appl. No.: 12/545,618

(22) Filed: Aug. 21, 2009

(65) Prior Publication Data

US 2010/0045048 A1    Feb. 25, 2010

Related U.S. Application Data

(60) Provisional application No. 61/090,700, filed on Aug. 21, 2008.

(51) Int. Cl.
*A61F 2/06* (2006.01)
*H02P 9/04* (2006.01)

(52) U.S. Cl. ........................ 290/1 R; 623/1.32

(58) Field of Classification Search .............. 290/1 R, 290/1 A, 43, 54; 623/1.32; 600/485
See application file for complete search history.

(56) References Cited

U.S. PATENT DOCUMENTS

| | | |
|---|---|---|
| 3,899,366 A | 8/1975 | Tajkowski |
| 3,906,960 A | 9/1975 | Lehr |
| 4,082,097 A | 4/1978 | Mann et al. |
| 4,166,470 A | 9/1979 | Neumann |
| 4,690,143 A | 9/1987 | Schroeppel |
| 5,431,694 A | 7/1995 | Snaper et al. |
| 5,702,303 A | 12/1997 | Takemoto et al. |
| 5,810,015 A | 9/1998 | Flaherty et al. |
| 6,198,645 B1 | 3/2001 | Kotowski et al. |
| 6,407,483 B1 | 6/2002 | Nunuparov et al. |
| 6,595,912 B2 | 7/2003 | Lau et al. |
| 6,936,994 B1 | 8/2005 | Gimlan |
| 7,003,350 B2 | 2/2006 | Denker et al. |
| 2003/0199955 A1 | 10/2003 | Struble et al. |
| 2004/0133069 A1 | 7/2004 | Shapland et al. |
| 2004/0172087 A1 | 9/2004 | Forsell |
| 2004/0211043 A1 | 10/2004 | Will |
| 2005/0027332 A1 | 2/2005 | Avrahami et al. |
| 2006/0009831 A1 | 1/2006 | Lau et al. |
| 2006/0136010 A1 | 6/2006 | Spelman et al. |
| 2006/0235263 A1 | 10/2006 | Jacobson et al. |

(Continued)

FOREIGN PATENT DOCUMENTS

WO    WO 2006/121818 A2    11/2006

(Continued)

OTHER PUBLICATIONS

Chicago (AFP); Extra heart energy can power pacemaker: researchers; Yahoo! News; Nov. 10, 2008.

(Continued)

*Primary Examiner* — Nicholas Ponomarenko
(74) *Attorney, Agent, or Firm* — Shay Glenn LLP

(57) ABSTRACT

An energy harvesting device is provided that may include any of a number of features. One feature of the energy harvesting device is that it is adapted for insertion into a human blood vessel for converting pulsatile pressure in the blood vessel into electrical energy. The energy harvesting device can provide electrical energy to another electronic or electromechanical on or in the human body. The energy harvesting device can include an electrostatic generator. Methods associated with use of the energy harvesting device are also covered.

23 Claims, 3 Drawing Sheets

U.S. PATENT DOCUMENTS

| | | | |
|---|---|---|---|
| 2006/0245140 | A1 | 11/2006 | Hunt et al. |
| 2007/0038238 | A1 | 2/2007 | Freeman et al. |
| 2007/0049789 | A1 | 3/2007 | Abrams |
| 2007/0066997 | A1 | 3/2007 | He et al. |
| 2007/0088402 | A1 | 4/2007 | Melvin |
| 2007/0156179 | A1 | 7/2007 | S.E. |
| 2007/0167988 | A1 | 7/2007 | Cernasov |
| 2007/0293904 | A1 | 12/2007 | Gelbart |
| 2008/0021505 | A1 | 1/2008 | Hastings et al. |
| 2008/0200963 | A1 | 8/2008 | Pless et al. |
| 2008/0277943 | A1 | 11/2008 | Donelan et al. |
| 2008/0278028 | A1 | 11/2008 | Donelan et al. |
| 2009/0171448 | A1* | 7/2009 | Eli .............................. 623/1.32 |
| 2009/0216292 | A1 | 8/2009 | Pless et al. |
| 2009/0326611 | A1 | 12/2009 | Gillbe |
| 2010/0228308 | A1 | 9/2010 | Cowan et al. |
| 2010/0298720 | A1* | 11/2010 | Potkay .......................... 600/485 |

FOREIGN PATENT DOCUMENTS

| | | |
|---|---|---|
| WO | WO 2007/102937 A2 | 9/2007 |

OTHER PUBLICATIONS

SIMM Technology; Technology page; http://www.implantgen.org/technology.htm; printed Nov. 25, 2008.

Meninger S. et al; Vibration-to-Electric Energy Conversion; vol. 9; No. 1; pp. 64-76; Feb. 2001.

Ballard et al.; Leg intramuscular pressures during locomotion in humans; J. Appl. Physiol.; vol. 84; No. 6; pp. 1976-1981; 1998.

Beeby et al.; Energy harvesting vibration sources for microsystems applications; Meas Sci Technol; vol. 17; pp. R175-R195; 2006.

Cook-Chennault et al.; Powering MEMS portable devices—a review of non-regenerative and regenerative power supply systems special emphasis on piezoelectric energy harvesting systems; Smart Mater. Struct.; 17 (2008) 043001; 33 pgs.

Görge et al.; Microgenerators for energy autarkic pacemakers and defibrillators: fact or fiction?; Herz26; No. 1; pp. 64-68; 2000.

Hagood et al.; Development of micro-hydraulic transducer technology; Presented at the 10th Int'l. Conference on Adaptive Structures and Technologies; pp. 71-81; Oct. 11-13, 1999.

Häusler et al.; Implantable physiolocical power supply with PVDF film; Ferroelectrics; vol. 60; pp. 277-282; 1984.

Kornbluh et al.; Electroelastomers: Applications of Dielectric Elastomer Transducers for Actuation, Generation and Smart Structures; Proc. SPIE Smart Structures and Materials: Industrial and Commercial Applications of Smart Structures Technologies; 4698; pp. 254-270; 2002.

Mateu et al; Review of energy harvesting techniques and applications for microelectronics; Proceedings of the SPIE Microtechnologies for the New Millenium; 15 pgs.; 2005.

Mitcheson et al.; Analysis of Optimized Micro-Generator Architectures for Self-Powered Ubiquitous Computers; Adjunct Proc. UBICOMP 2002, 4th Int. Conf. Ubiquitous Computing; Gothenburg, Sweden; p. 5-6; Oct. 2002.

Mitcheson et al.; Architectures for Vibration-Driven Micropower Generators; J Microelectromechanical Systems; 13(3); pp. 429-440; Jun. 2004.

Mitcheson et al.; MEMS electrostatic micropower generator for low frequency operation; Sensors and Actuators A; vol. 115; pp. 523-529; 2004.

Morrow, D.; Microsensor for intramuscular pressure measurement (2003); Mayo Clinic; http://mayoresearch.mayo.edu/mayo/research/biomechanics/muscle_mech2cfm; (accessed: Oct. 19, 2009).

Myers et al.; Biologically-energized cardiac pacemaker; IEEE Transactions on Bio-Medical Electronics (letters to the Editor); vol. BME-10; No. 2; p. 83; Apr. 1963.

Paradiso; Energy harvesting for mobile computing (presentation); Responsive Environments Group, MIT Media Lab; 54 pgs.; Jun. 2005.

Platt; Electric power generation within orthopaedic implants using piezoelectric ceramics; Masters Thesis; 92 pgs.; 2003.

Reilly et al.; Thin film piezoelectric energy scavenging systems for long term medical monitoring; Proceedings of the Int'l Workshop on Wearable and Implantable Body Sensor Networks (BSN'06); pp. 38-41; Apr. 3-5, 2006.

Sjøgaard et al.; Intramuscular pressure and EMG relate during static contractions but dissociate with movement and fatigue; J Appl Physiol; vol. 96; pp. 1522-1529; 2004.

Teng et al.; Compressive loading on bone surfaces from muscular contraction: an in vivo study in the miniature pig, sus scrofa; Journal of Morphology; vol. 238; pp. 71-80; 1998.

Torres et al.; Electrostatic energy harvester and Li-Ion charger circuit for micro-scale applications; MWSCAS '06, 49th IEEE Int'l. Midwest Symposium on Circuits and Systems; pp. 65-69; Aug. 6-9, 2006.

\* cited by examiner

DEVICE FOR ENERGY HARVESTING WITHIN A VESSEL

CROSS REFERENCE TO RELATED APPLICATIONS

This application claims the benefit under 35 U.S.C. 119 of U.S. Provisional Patent Application No. 61/090,700, filed Aug. 21, 2008, titled "DEVICE FOR ENERGY HARVESTING WITHIN A VESSEL." This application is herein incorporated by reference in its entirety.

INCORPORATION BY REFERENCE

All publications and patent applications mentioned in this specification are herein incorporated by reference to the same extent as if each individual publication or patent application was specifically and individually indicated to be incorporated by reference.

FIELD OF THE INVENTION

This invention relates generally to the power generation field, and more specifically to new and useful devices, methods, and systems for harvesting energy.

BACKGROUND OF THE INVENTION

Implantable medical devices, such as implantable pulse generators like neurostimulators, spinal cord stimulators, or pacemakers, require a power supply to generate a pulse or stimulation. Conventional stimulators typically have either large batteries that are uncomfortable for the patient, or smaller batteries that require frequent recharging. Additionally, for example, conventional Cardiac Resynchronization Therapy (CRT) Implantable Cardioverter Defibrillators (ICDs) stimulate the heart frequently and as a result have a high current drain from the battery and typically only last a few years before they need to be replaced due to battery depletion.

Thus there is a need in the implantable medical devices field for an alternative source of power for these devices, allowing these devices to be smaller and/or not require recharging or frequent recharging. Such improvements might significantly increase the longevity of these implantable medical devices resulting in improved patient care and reduced cost.

The various illustrative embodiments described herein provide an alternative source of power for these devices or other suitable devices or machines. Described herein are new and useful devices, methods, and systems for harvesting energy.

SUMMARY OF THE INVENTION

One aspect of the invention includes an energy harvesting device, comprising a body adapted to be inserted into a blood vessel, a central lumen configured allow for a largely unimpeded flow of blood, and an energy harvesting generator disposed in the body, the energy harvesting generator adapted to convert pressure variations in the central lumen into electrical energy.

In some embodiments, the energy harvesting generator is an electrostatic generator. The electrostatic generator can comprise a capacitor having a high pressure state and a low pressure state. In some aspects of the invention, electrical energy can be harvested from the capacitor upon a change from the high pressure state to the low pressure state. In other embodiments, electrical energy can be harvested from the capacitor upon a change from the low pressure state to the high pressure state.

In some aspects of the invention, the energy harvesting generator can further comprise a membrane in fluid communication with the blood, an outer wall not in fluid communication with the blood, a first electrical conductor disposed between the membrane and the outer wall, a second electrical conductor disposed between the first electrical conductor and the outer wall, and a fluid disposed between the first and second electrical conductors.

In some embodiments, the energy harvesting generator includes a high pressure state and a low pressure state, wherein electrical energy is harvested from the energy harvesting generator upon a change from the high pressure state to the low pressure state. In other embodiments, electrical energy is harvested from the energy harvesting generator upon a change from the low pressure state to the high pressure state.

In some embodiments, the fluid disposed between the first and second electrical conductors can have a low dielectric constant. The fluid can be an oil, for example. In some embodiments, the first electrical conductor can be a conductive film disposed on the membrane and the second electrical conductor can be a metallic foil. The metallic foil can comprise titanium or stainless steel, for example. In additional embodiments, an insulator can be disposed on an outer surface of the metallic foil. The insulator can comprise barium titanate, for example. In even additional embodiments, the energy harvesting device can further comprise a gas filled expansion space disposed between the second electrical conductor and the outer wall.

In one aspect of the invention, the energy harvesting device is configured to be inserted into a human vessel. The body can have an outer diameter of approximately 10 to 50 mm and a length of approximately 10 to 100 mm, for example.

Another aspect of the invention is a method of harvesting energy from a blood vessel, comprising inserting an elongate body into a blood vessel, allowing blood to flow largely unimpeded through the elongate body, and generating electrical energy from the pressure variations caused by blood flow through the elongate body. In some embodiments, the electrical energy is generated by an energy harvesting generator. The energy harvesting generator can comprise a capacitor having a high pressure state and a low pressure state. In some embodiments, electrical energy can be harvested from the capacitor upon a change from the high pressure state to the low pressure state. In another embodiment, electrical energy can be harvested from the capacitor upon a change from the low pressure state to the high pressure state. The energy harvesting generator can form a high value capacitor during the high pressure state and a low value capacitor during the low pressure state.

Another aspect of the invention provides a method of harvesting energy from a blood vessel, comprising inserting an energy harvesting device into a blood vessel, and generating electrical energy with the energy harvesting device from pulsatile pressure in the blood vessel.

BRIEF DESCRIPTION OF THE DRAWINGS

The novel features of the invention are set forth with particularity in the claims that follow. A better understanding of the features and advantages of the present invention will be obtained by reference to the following detailed description

DETAILED DESCRIPTION OF THE INVENTION

Figure 1:
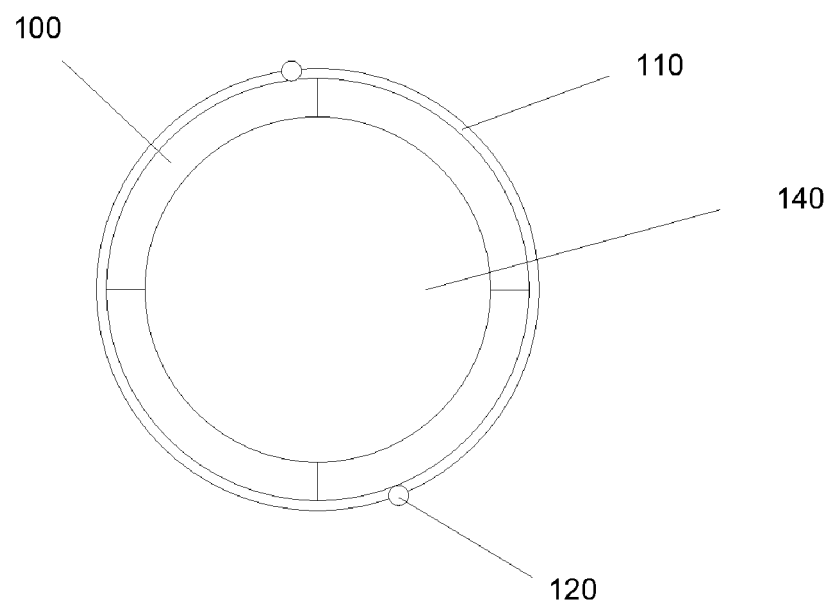
FIG. 1 shows a radial cross section of a stent or stent-like device incorporating an energy harvesting circuit.

FIG. 1 shows a radial cross section of a stent or stent-like device incorporating an energy harvesting circuit. The device has an outer structure 110 that is like a stent and intended to locate on the inner lumen of a naturally occurring body vessel such as an artery. The outer structure 110 is sized to fit in the major blood vessels of the body and is preferably on the order of 0.25 to 4.0 centimeters in diameter. The central lumen 140 allows largely unimpeded flow of arterial blood. There are several compartments 100 that can be used to house electronic devices such as stimulators for stimulating nerves or tissue such as cardiac or pulmonary tissue. Such compartments 100 would be on the order of 100 cubic millimeters in volume to accommodate the electronic devices. Electrodes 120 are disposed on the surface to contact tissue for the purposes of electrical stimulation. The electrical stimulation may be of the sympathetic or parasympathetic system to treat hypertension, pain, headache, inflammation, diabetes, and metabolic and gastric disorders or other disorders susceptible to neural stimulation. The compartments 100 may also be used to house energy harvesting generators such as the one shown in FIG. 3 adapted to convert naturally occurring pressure variations in the central lumen 140 into electrical energy.

Figure 2:
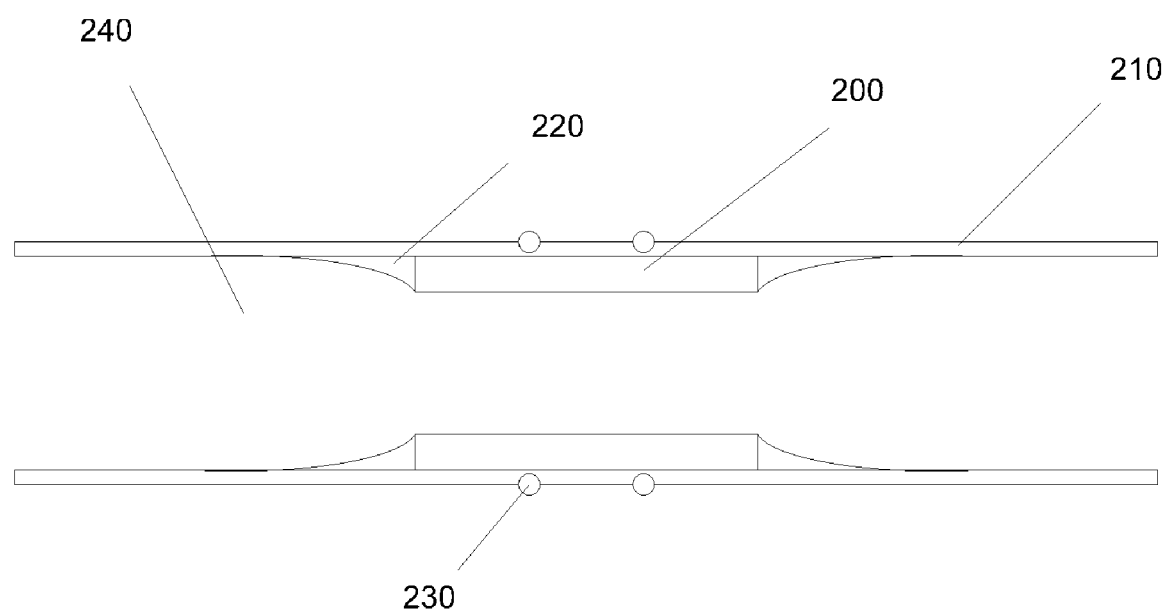
FIG. 2 shows a longitudinal cross section of a stent or stent-like device incorporating an energy harvesting circuit.

FIG. 2 shows a longitudinal cross section of a representative embodiment. The outer wall 210 is a stent or stent-like structure intended to locate on the inner surface of a naturally occurring body vessel such as an artery. Depending on the vessel into which the device is deployed, the length may be of the order of one to ten centimeters. A central lumen 240 allows for the largely unimpeded flow of arterial blood. Compartments 200 are shown in cross section, some of which may be used to house electronics to implement nerve or cardiac stimulators (for example) and some of which may be used to house an energy harvesting generator as depicted in FIG. 3.

Figure 3:
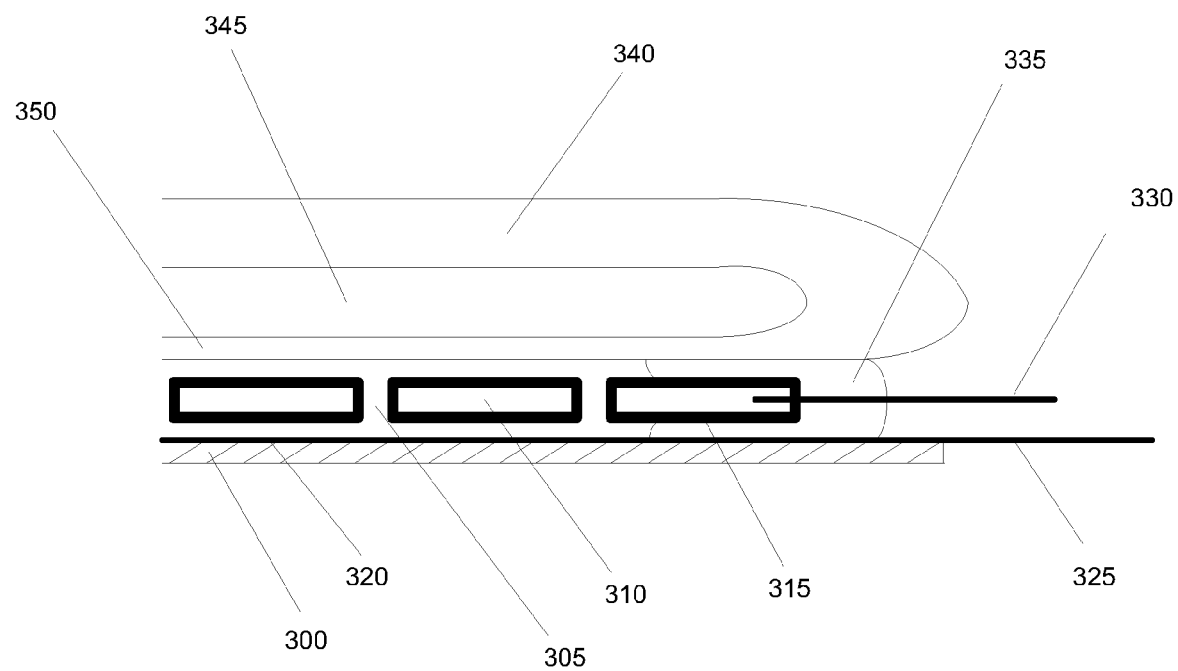
FIG. 3 shows a cross section of an electrostatic generator adapted for use in a stent or stent-like device.

FIG. 3 shows a cross section of an embodiment of an electrostatic generator suitable for use in a stent or stent-like device inserted into the arterial system of a patient (or other animal). A membrane 300 preferably fabricated of a thin polymer is in contact with a patient's blood, and receives pressure variations from the patient's blood. Such pressure variations are typically on the order of 40 millimeters of mercury each cardiac cycle. On the side of the membrane 300 not in contact with the patient's blood is an electrically conducting film 320. The film 320 is typically deposited on the membrane 300. A pierced metal foil 310 has apertures 305 that are filled with a fluid having a low dielectric constant such as an oil. The metal foil 310 may be made of titanium, stainless steel or any other suitable conductor. On the surface of the metal foil 310 is a thin coating of an insulator 315. The insulator 315 is preferably made from a material having a high dielectric constant such as barium titanate. On the other side of the foil 310 from the membrane 300 is a compliant separator 350 backed by a gas filled expansion space 345 that is further contained by a comparatively rigid wall 340. The gas may be any suitable gas such as air, nitrogen or argon. The space between the separator 350 and the membrane 300 is sealed at edges with an adhesive 335 or equivalent. Two electrically conducting wires 330 and 325 connect to the conductive film 320 and the foil 310.

In operation, when the pressure in the arterial vessel increases, the membrane 300 with its conductive foil backing 320 displaces the dielectric fluid and is pressed up against the insulating coating 315 of the foil 310. Under these circumstances (the high pressure state), a comparatively high value capacitor is formed having the foil 310 and the conductive membrane 320 as its electrodes, and the high dielectric constant insulator 315 as the dielectric. During the high pressure state, a force is transmitted to the separator 350 by the dielectric fluid causing it to bulge into the compliance space 345 compressing the gas within. When the arterial pressure subsides (the low pressure state), the spring force of the compressed gas in the compliance space 345 and the distended separator 350 puts a force on the dielectric fluid that pushes the membrane 300 and the foil layer 320 away from metal foil 310 and the insulating layer 315. During the low pressure state, a comparatively low value capacitor is formed not only because the plates of the capacitor (320 and 310) are further apart, but also because the low dielectric fluid is now between the plates (320 and 310) dropping the capacitance dramatically.

The electrical cycle to harvest energy from an electrostatic generator is well known and is briefly reviewed here. During the high pressure state the capacitance is high and a low voltage (the "seed" voltage) is imposed on the capacitor. During the low pressure state the capacitance drops and the voltage on the capacitor increases allowing energy to be harvested. With this device energy may be harvested in amounts suitable to power a low-powered stimulator which may require on the order of 100 microwatts to function.

In this embodiment the foil 310 is one plate of the capacitor and the conductive film 325 on the membrane 300 is the other plate. An alternative configuration that may be preferred is to have the conductive film 320 on the separator 350. A further configuration would be to have conductive film 320 on both the separator 350 and the membrane 300 allowing energy harvesting both on transition from the low pressure state to the high pressure state and the high pressure state to the low pressure state.

In operation an energy harvester (an embodiment of which is shown in FIG. 3) is used to power circuits contained in housings (100 and 200) of the device that is placed in a naturally occurring body lumen such as an artery. The device may further include communications circuits for the implanted device to communicate with an external clinical controller for setting operating parameters and transmitting data such as the pressure in the lumen. The energy harvester in the device provides power (at least in part) for the electronic or electromechanical device in the stent or stent-like structure. The electronic or electromechanical device may be, without limitation, a neurostimulator, a pacemaker, drug pump, or a sensor such as a pressure, flow, temperature, optical, glucose, genetic or cellular sensor. The device may be implanted in a range of vessels including (without limitation) the aorta, the pulmonary vessels, the carotid, and the hepatic and renal artery to treat hypertension, asthma, COPD, and to improve cardiac contractility and diabetes.

As for additional details pertinent to the present invention, materials and manufacturing techniques may be employed as within the level of those with skill in the relevant art. The same may hold true with respect to method-based aspects of the invention in terms of additional acts commonly or logically employed. Also, it is contemplated that any optional feature of the inventive variations described may be set forth and claimed independently, or in combination with any one or more of the features described herein. Likewise, reference to a singular item, includes the possibility that there are plural of the same items present. More specifically, as used herein and in the appended claims, the singular forms "a," "and," "said," and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation. Unless defined otherwise herein, all technical and scientific terms used herein have the same meaning as commonly understood by one of ordinary skill in the art to which this invention belongs. The breadth of the present invention is not to be limited by the subject specification, but rather only by the plain meaning of the claim terms employed.

What is claimed is:

1. An energy harvesting device, comprising:
   a body adapted to be inserted into a blood vessel;
   a central lumen configured allow for a largely unimpeded flow of blood; and
   an energy harvesting generator disposed in the body, the energy harvesting generator adapted to convert pressure variations in the central lumen into electrical energy.

2. The energy harvesting device of claim 1 wherein the energy harvesting generator is an electrostatic generator.

3. The energy harvesting device of claim 2 wherein the electrostatic generator comprises a capacitor having a high pressure state and a low pressure state.

4. The energy harvesting device of claim 3 wherein electrical energy is harvested from the capacitor upon a change from the high pressure state to the low pressure state.

5. The energy harvesting device of claim 1 wherein the energy harvesting generator further comprises:
   a membrane in fluid communication with the blood;
   an outer wall not in fluid communication with the blood;
   a first electrical conductor disposed between the membrane and the outer wall;
   a second electrical conductor disposed between the first electrical conductor and the outer wall; and
   a fluid disposed between the first and second electrical conductors.

6. The energy harvesting device of claim 5 wherein the energy harvesting generator includes a high pressure state and a low pressure state, wherein electrical energy is harvested from the energy harvesting generator upon a change from the high pressure state to the low pressure state.

7. The energy harvesting device of claim 5 wherein the fluid has a low dielectric constant.

8. The energy harvesting device of claim 5 wherein the fluid is an oil.

9. The energy harvesting device of claim 5 wherein the first electrical conductor is a conductive film disposed on the membrane.

10. The energy harvesting device of claim 5 wherein second electrical conductor is a metallic foil.

11. The energy harvesting device of claim 10 wherein the metallic foil comprises titanium.

12. The energy harvesting device of claim 10 wherein the metallic foil comprises stainless steel.

13. The energy harvesting device of claim 10 wherein an insulator is disposed on an outer surface of the metallic foil.

14. The energy harvesting device of claim 13 wherein the insulator comprises barium titanate.

15. The energy harvesting device of claim 5 further comprising a gas filled expansion space disposed between the second electrical conductor and the outer wall.

16. The energy harvesting device of claim 1 wherein the body has an outer diameter of approximately 10 to 50 mm.

17. The energy harvesting device of claim 1 wherein the body has a length of approximately 10 to 100 mm.

18. A method of harvesting energy from a blood vessel, comprising:
   inserting an elongate body into a blood vessel;
   allowing blood to flow largely unimpeded through the elongate body; and
   generating electrical energy from the pressure variations caused by blood flow through the elongate body.

19. The method of claim 18 wherein the electrical energy is generated by an energy harvesting generator.

20. The method of claim 19 wherein the energy harvesting generator comprises a capacitor having a high pressure state and a low pressure state.

21. The method of claim 20 wherein electrical energy is harvested from the capacitor upon a change from the high pressure state to the low pressure state.

22. The method of claim 20 wherein further comprising forming a high value capacitor during the high pressure state and a low value capacitor during the low pressure state.

23. A method of harvesting energy from a blood vessel, comprising:
   inserting an energy harvesting device into a blood vessel; and
   generating electrical energy with the energy harvesting device from pulsatile pressure in the blood vessel.

* * * * *